United States Patent [19]

Mino

[11] Patent Number: 5,788,656
[45] Date of Patent: Aug. 4, 1998

[54] ELECTRONIC STIMULATION SYSTEM FOR TREATING TINNITUS DISORDERS

[76] Inventor: Alfonso Di Mino, 15 Arcadia Rd., Woodcliff Lake, N.J. 07675

[21] Appl. No.: 808,180

[22] Filed: Feb. 28, 1997

[51] Int. Cl.$^6$ .................................................. A61H 1/00
[52] U.S. Cl. .................................................. 601/47
[58] Field of Search .................... 128/897; 600/559, 600/27, 28; 601/46, 47, 48, 78, 79, 80, 81, 9; 607/55

[56] References Cited

U.S. PATENT DOCUMENTS

| | | | |
|---|---|---|---|
| 717,407 | 12/1902 | Hutchison | 601/78 |
| 2,062,372 | 12/1936 | Nicolides | 601/79 |
| 4,222,393 | 9/1980 | Hocks et al. | 600/559 |
| 5,167,239 | 12/1992 | Junker | 600/559 |
| 5,403,262 | 4/1995 | Gooch | 607/55 |

Primary Examiner—William E. Kamm
Attorney, Agent, or Firm—Michael Ebert

[57] ABSTRACT

An electronic stimulation system for treating a patient suffering from a tinnitus disorder in which the patient hears ringing or other sounds originating in the ear. The system includes an electronically actuated probe to which is applied a complex signal in the auditory range to cause the probe to vibrate in accordance with the signal. The probe is placed at a site on the patient in proximity to the cochlea of the inner ear whereby the probe vibrations are transmitted to the cochlea to stimulate this organ and thereby alleviate the tinnitus disorder. In this system, use is made of two adjustable audio-frequency oscillators, one operating in a low frequency range whose upper limit is about 400 Hz, the other operating in a high-frequency whose upper limit is about 1000 Hz. The outputs of these oscillators are combined and amplified to produce the complex signal applied to the probe. The mechanical vibrations transmitted by the probe in accordance with the complex signal must be properly related to the sonic frequencies of the tinnitus sounds being heard by the patient.

6 Claims, 1 Drawing Sheet

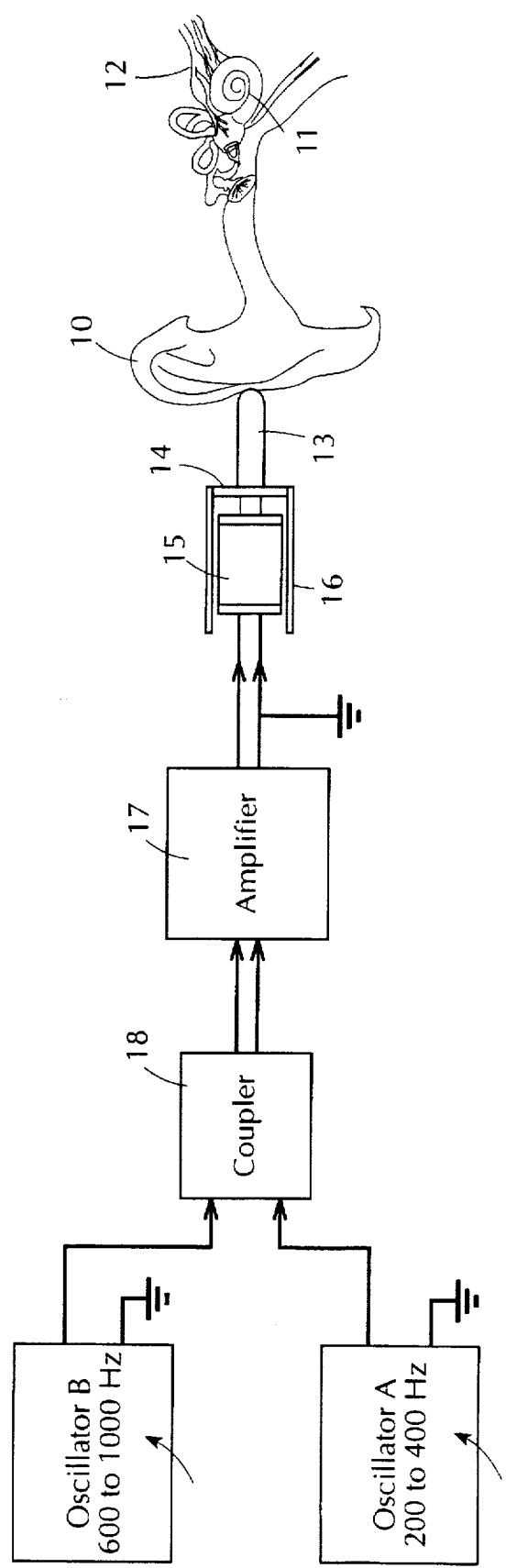

ELECTRONIC STIMULATION SYSTEM FOR TREATING TINNITUS DISORDERS

BACKGROUND OF INVENTION

1. Field of Invention:

This invention relates generally to the treatment of tinnitus disorders, and more particularly to an electronic stimulation system in which a complex signal in the audio range is applied to an electromagnetically actuated probe to cause the probe to vibrate in accordance with the signal, the vibrations of the probe being transmitted to the cochlea of the inner ear of a patient to stimulate this organ and thereby alleviate the tinnitus disorder suffered by the patient.

2. Status of Prior Art:

The human ear functions as an auditory system for converting incoming sound vibrations into electrical energy which triggers nerve impulses in the auditory nerve connected to the brain. In this auditory system, sounds picked up by the outer ear (auriole) are conducted through an auditory canal to a tympanic membrane or eardrum. The middle ear which is separated from the outer ear by the eardrum, contains three small bones which as sounds strike the eardrum are then caused to vibrate. These bone vibrations set up corresponding vibrations in an oval window from which the vibrations are conveyed to the three fluid-filled canals contained in the cochlea of the inner ear.

At the base of the central canal of the cochlea is a basilar membrane, and supported on this membrane is the organ of Corti and its hair cells. These cells are the true receptors of hearing, for proliferations from the fibers of the auditory nerve extend up the center of the cochlea and connect with these hair cells.

Auditory sounds vary in frequency throughout the audio spectrum. The ability to hear many different frequencies as distinct pitches is related to the ability of the cochlea to resolve these frequencies. In the range of about 200 to 2000 Hz, this resolution is effected by differential response of the basilar membrane. The cochlea has different resonance values at different points along its length. Hence high tones cause the fluid of the cochlea and the membrane to vibrate near the base, while low tones cause these to vibrate near the apex.

The concern of the present invention is with the treatment of tinnitus disorders. Tinnitus aureum, in Latin, literally means "ringing of the ears" and is a common symptom in adults. Though the term refers to sounds originating in the ear, they may not be ringing in nature, for buzzing, humming, whistling and roaring sounds are also indicative of a tinnitus disorder.

A more precise definition of tinnitus is any sound sensation for which there is no source outside of the individual. According to the text *Principles of Neurology* by Adams & Victor—McGraw Hill (Third Edition), "For most forms of tinnitus, there is little effective treatment." Yet despite this negative approach to tinnitus, the prior art discloses various attempts to overcome this condition.

Thus the Westerman U.S. Pat. No. 5,325,872 (1994) there is shown an electronic system for treating tinnitus in which the outputs of two voltage-controlled oscillators operating in the sonic range are combined and amplified. The resultant signal is applied to an ear piece placed on the outer ear of the patient. Hence what the patient hears is a therapeutic tone whose frequency repeatedly and slowly scans throughout a frequency range which contains the tinnitus ringing tone. According to Westerman, because the therapeutic tone with each scan repeats the ringing frequency, this acts to mask or suppress the ringing frequency.

A similar approach is taken by Gooch in U.S. Pat. No. 5,403,262 (1995) in which applied to the ear of a patient suffering from a tinnitus ringing sound is a tone of a frequency which masks the tinnitus ringing sound and overrules this sound.

The effectiveness of these prior approaches is believed to be of limited value in the treatment of tinnitus in that the therapeutic tone is applied to the outer ear of the patient and does not therefore adequately operate on the nerve cells responsible for the tinnitus condition.

In the nerve center associated with the brain which is responsible for processing sounds, each individual nerve cell located in the uppermost level of the eighth cranial nerve is stimulated only by a sound having a specific frequency. It is therefore the task of the multitude of nerve cells in the uppermost level of the eighth nerve to inform the brain that specific sounds or tones are being heard, or that a complex tone or a mixture of sounds are being heard. Hence each nerve cell in the nerve center has an assigned task.

The reason therefore a patient suffering from tinnitus has the sensation of hearing a ringing tone made up of specific frequencies is that the nerve cells that normally hear and transmit to the brain a really audible tone composed of these frequencies are being artificially stimulated, and may remain in this condition for a prolonged period. The cause of this faulty stimulation is not known, but what is known is that a substantial percentage of adults throughout the world suffer from tinnitus.

Inasmuch as the nerve center associated with the brain is the source of tinnitus disorders, and in the human auditory system it is the cochlea that conducts impulses to this nerve center, in a system in accordance with the invention to treat tinnitus, it is the cochlea that is stimulated.

SUMMARY OF INVENTION

In view of the foregoing, the main object of this invention is to provide an electronic stimulation system for treating a patient suffering from a tinnitus disorder; the system acting to transmit vibrations in the sonic range to the cochlea of the inner ear.

More particularly, an object of this invention is to provide a system of the above type which includes an electromagnetically actuated probe to which is applied a complex signal in the auditory range to cause the probe to vibrate in accordance with the signal, the probe being placed at a position on the patient in proximity to the cochlea of the inner ear whereby the probe vibrations are transmitted to the cochlea.

Briefly stated, these objects are attained by an electronic stimulation system for treating a patient suffering from a tinnitus disorder in which the patient hears ringing or other sounds originating in the ear. The system includes an electronically actuated probe to which is applied a complex signal in the auditory range to cause the probe to vibrate in accordance with the signal. The probe is placed at a site on the patient in proximity to the cochlea of the inner ear whereby the probe vibrations are transmitted to the cochlea to stimulate this organ and, thereby alleviate the tinnitus disorder.

In this system use is made of two adjustable audio-frequency oscillators, one operating in a low-frequency range whose upper limit is about 400 Hz, the other operating in a high-frequency whose upper limit is about 1000 Hz. The outputs of these oscillators are combined and amplified to produce the complex signal which is applied to the probe. The mechanical vibrations transmitted by the probe in accordance with the complex signal must be properly related to the sonic frequencies of the tinnitus sounds being heard by the patient.

BRIEF DESCRIPTION OF DRAWING

For a better understanding of the invention reference is made to the attached drawing whose single figure is a block diagram of an electronic stimulation system for treating a patient suffering from a tinnitus disorder.

DESCRIPTION OF INVENTION

Referring now to the drawing, shown therein schematically is a patient 10 to be treated who is suffering from a tinnitus condition. The auditory system of the patient includes an inner ear provided with a cochlea 11 connected to a cochlear nerve 12 leading to the eighth cranial nerve.

The spiral ganglion of the cochlea is composed of bipolar cells, the peripheral processes of which convey auditory impulses from the specialized neuroepithelium of the inner ear which is the spiral organ of Corti, the end organ of hearing. The Corti consists of numerous hair cells aligned in rows along the 2½ turns of the cochlea.

In a system in accordance with the invention, pressed against the body of patient 10 at a site in the proximity of cochlea 11 is a probe 13 which is anchored on a diaphragm 14 and projects therefrom. Diaphragm 14 is mounted at the end of a tubular casing 16 and is electromagnetically actuated by a solenoid 15 housed within the casing.

Applied to solenoid 15 is a complex signal in the audio range yielded by an amplifier 17 whereby diaphragm 14 and probe 13 coupled thereto are caused to vibrate vigorously in accordance with the signal. These vibrations are transmitted through the tissue between the probe and the cochlea to the cochlea and act to so stimulate the cochlea as to cause the tinnitus condition to be alleviated. With repeated treatments, the tinnitus condition will be substantially reduced or eliminated.

To generate the complex signals, two oscillators A and B are provided. Oscillator A, whose frequency is adjustable, generates a frequency in the low-frequency sonic range of 200 to 400 Hz. Oscillator B, whose frequency is adjustable, generates a frequency in the high-frequency sonic range of 600 to 1000 Hz. The outputs of oscillators A and B are combined in a coupler 18 which may be resistive or capacitive network the output of which is applied to amplifier 18. In practice, amplifier 18 may be a 10 watt amplifier whose output volume is adjustable. The complex signal yielded by the amplifier includes the low and high frequencies of the oscillators and the positive and negative beats of these frequencies.

In order to effectively treat the particular tinnitus conditions from which patient 10 suffers, the mechanical vibrations transmitted by probe 13 to cochlea 11 which are in accordance with the complex signal, must be properly related to the sonic frequencies of the tinnitus sounds being heard by patient 10.

Since it is only the patient who hears the internally-generated tinnitus sounds, the patient himself must determine which vibratory frequencies transmitted to the cochlea by probe 13 are effective. To this end, the patient who is hearing these tinnitus sounds, adjusts the settings of oscillators A and B within their respective low and high frequency sonic ranges until he finds settings at which the resultant complex signal acts to mask or interfere with the tinnitus sounds he is hearing. To carry out this operation, the volume of amplifier 17 is turned down so that the patient can clearly hear the tinnitus sound as he listens to the sounds stimulated in the cochlea by the vibrations of the probe, for the cochlea translates these vibrations into sounds. When the patient finds settings for oscillators A and B which result in a complex signal that interferes with the tinnitus sounds, the system is then ready for treatment and the amplifier volume is then turned up for this purpose.

Each treatment is conducted for 2 to 5 minutes and is repeated at least twice a day until the tinnitus disorder suffered by the patient is substantially reduced or eliminated.

Principles of Operation:

As pointed out previously, a tinnitus condition is due to the artificial stimulation of particular nerve cells in the nerve center associated with the brain responsible for processing sounds, each nerve cell having an assigned frequency. Though the cause of this faulty stimulation is not known, what a patient does know is the sonic nature of the ringing sounds, for he hears these sounds.

The ringing sounds are not composed of a steady tone, but of a tone which in musical terms would be referred to as a vibrato. Thus the basic ringing tone is relatively high sonic frequency, this being modulated by a sonic tone of lower frequency. Hence the nerve cells which are artificially stimulated to produce ringing sounds are those nerve cells whose assigned frequencies are such as that together they recreate the ringing sounds.

In a system in accordance with the invention, the complex signal is composed of a high-frequency sonic tone modulated by a low-frequency sonic tone. This signal serves to electromagnetically actuate the probe to produce vibrations whose repetition rates correspond to the frequencies of the complex signal, which frequencies are similar to those which make up the ringing sounds.

The vibrations transmitted by the probe to the cochlea act to shock excite the nerve cells responsible for the tinnitus condition and act to restore these cells to a normal state in which the cells are no longer subject to artificial stimulation and therefore no longer produce tinnitus sounds.

While there has been shown and described an electronic stimulation system for treating tinnitus disorders in accordance with the application, it will be appreciated that many changes and modifications may be made therein without, however, departing from the essential spirit thereof.

We claim:

1. An electronic stimulation system for treating a patient having a tinnitus condition in which he hears ringing or other sounds in the sonic frequency range, the sounds heard internally by the patient having predetermined frequencies, said system comprising:

A. means to generate a complex electrical signal having frequency components lying with said sonic range, said means being adjustable by the patient to yield frequency components which interfere with the frequencies of the tinnitus sounds heard by the patient;

B. means to produce mechanical vibrations corresponding to said complex signal; and C. means to apply said mechanical vibrations to a site on said patient in the proximity of the cochlea of his inner ear whereby the vibrations are transmitted to the cochlea to relieve the tinnitus condition.

2. A system as set forth in claim 1, in which the means to produce said mechanical vibrations includes a diaphragm and means to electromagnetically actuate the diaphragm in accordance with said complex signal.

3. A system as set forth in claim 2, in which the means to apply said vibrations to the patient includes a probe anchored on said diaphragm.

4. A system as set forth in claim 1, in which the means to generate the complex signal are constituted by a low sonic frequency oscillator which is adjustable in frequency and a high sonic frequency oscillator which is adjustable in frequency, and means to combine the adjusted outputs of said low and high-frequency oscillators to produce the complex signal having the desired frequency components.

5. A system as set forth in claim 4, in which the low-frequency oscillator is adjustable in a range whose upper limit is about 400 Hz.

6. A system as set forth in claim 4, in which the high-frequency oscillator is adjustable in a range whose upper limit is about 1000 Hz.

* * * * *